US009603697B2

(12) United States Patent
Centola

(10) Patent No.: US 9,603,697 B2
(45) Date of Patent: Mar. 28, 2017

(54) ONE-PIECE BIFURCATION GRAFT

(75) Inventor: Marcos Centola, CEP São José do Rio Preto (BR)

(73) Assignee: JOTEC GMBH, Hechingen (DE)

(*) Notice: Subject to any disclaimer, the term of this patent is extended or adjusted under 35 U.S.C. 154(b) by 599 days.

(21) Appl. No.: 13/361,498

(22) Filed: Jan. 30, 2012

(65) Prior Publication Data

US 2012/0150273 A1    Jun. 14, 2012

Related U.S. Application Data

(63) Continuation of application No. PCT/EP2009/005552, filed on Jul. 31, 2009.

(51) Int. Cl.

| A61F 2/954 | (2013.01) |
|---|---|
| A61F 2/07 | (2013.01) |
| A61F 2/848 | (2013.01) |
| A61F 2/06 | (2013.01) |
| A61F 2/89 | (2013.01) |
| A61F 2/90 | (2013.01) |

(52) U.S. Cl.
CPC ............... *A61F 2/07* (2013.01); *A61F 2/954* (2013.01); *A61F 2/848* (2013.01); *A61F 2/89* (2013.01); *A61F 2/90* (2013.01); *A61F 2002/061* (2013.01); *A61F 2002/065* (2013.01); *A61F 2002/072* (2013.01); *A61F 2230/0078* (2013.01)

(58) Field of Classification Search
CPC .... A61F 2/07; A61F 2/848; A61F 2/89; A61F 2/90; A61F 2/954; A61F 2002/061; A61F 2002/072; A61F 2002/065; A61F 2230/0078; A61F 2/962; A61F 2/966; A61F 2002/9534; A61F 2002/9511; A61F 2002/9665

USPC ............... 623/1.11, 1.12, 1.15, 1.16
See application file for complete search history.

(56) References Cited

U.S. PATENT DOCUMENTS

| 2,845,959 A | 8/1958 | Sidebotham |
|---|---|---|
| 5,824,055 A * | 10/1998 | Spiridigliozzi ......... A61F 2/966 606/195 |

(Continued)

FOREIGN PATENT DOCUMENTS

| FR | 2874500 | 3/2006 |
|---|---|---|
| JP | 08-047503 | 2/1996 |

(Continued)

OTHER PUBLICATIONS

International Search Report and Written Opinion mailed Jul. 16, 2010, from parent International Patent Application No. PCT/EP2009/005552.

(Continued)

*Primary Examiner* — Christopher L Templeton
*Assistant Examiner* — Lucas Paez
(74) *Attorney, Agent, or Firm* — Casimir Jones, SC

(57) ABSTRACT

The present invention relates to an endoluminal prosthesis to be deployed at a vessel bifurcation, comprising a one-piece graft sleeve with a branching portion, defining a first prosthesis lumen and having, in its deployed state, a first diameter, said branching portion being reinforced by stent elements, and a trunk portion, defining a second prosthesis lumen in fluid communication with said first prosthesis lumen and having, in its deployed state, a second diameter. The trunk portion is essentially free from reinforcing stent-material (FIG. 4).

8 Claims, 10 Drawing Sheets

(56) References Cited

U.S. PATENT DOCUMENTS

| | | | |
|---|---|---|---|
| 6,432,131 B1 | 8/2002 | Ravenscroft | |
| 6,517,572 B2 * | 2/2003 | Kugler et al. | 623/1.13 |
| 6,773,457 B2 * | 8/2004 | Ivancev et al. | 623/1.28 |
| 6,808,534 B1 * | 10/2004 | Escano | 623/1.23 |
| 7,122,048 B2 | 10/2006 | DiMatteo et al. | |
| 7,823,267 B2 * | 11/2010 | Bolduc | 29/525.01 |
| 2003/0167087 A1 * | 9/2003 | Piplani et al. | 623/1.35 |
| 2003/0208256 A1 | 11/2003 | DiMatteo et al. | |
| 2004/0111145 A1 | 6/2004 | Serino et al. | |
| 2004/0138734 A1 * | 7/2004 | Chobotov et al. | 623/1.11 |
| 2006/0241740 A1 * | 10/2006 | Vardi | A61F 2/82 623/1.16 |
| 2008/0221655 A1 * | 9/2008 | Miller | A61F 2/856 623/1.11 |
| 2009/0043377 A1 * | 2/2009 | Greenberg | A61F 2/07 623/1.35 |
| 2009/0171451 A1 | 7/2009 | Kuppurathanam et al. | |
| 2009/0287145 A1 * | 11/2009 | Cragg et al. | 604/96.01 |

FOREIGN PATENT DOCUMENTS

| | | |
|---|---|---|
| WO | 00/53251 | 9/2000 |
| WO | 00/64355 | 11/2000 |
| WO | 03/009773 | 2/2003 |
| WO | 2004/037116 | 5/2004 |
| WO | 2004/047682 | 6/2004 |
| WO | 2005/037076 | 4/2005 |
| WO | 2009/137069 | 11/2009 |

OTHER PUBLICATIONS

English translation of Jun. 18, 2013 Notification of Reasons for Rejection for JP Patent Application No. 2012-521969.

* cited by examiner

ONE-PIECE BIFURCATION GRAFT

CROSS REFERENCES TO RELATED APPLICATIONS

This application is a continuation of international patent application PCT/EP2009/005552, filed on Jul. 31, 2009 and designating the U.S., which international patent application has been published in English language. The entire content of these priority applications is incorporated herein by reference.

BACKGROUND OF THE INVENTION

The present invention relates to an endoluminal prosthesis to be deployed at a vessel bifurcation, comprising a one-piece graft sleeve, said graft sleeve having a branching portion, defining a first prosthesis lumen, said branching portion having, in its deployed state, a first diameter and being reinforced by stent elements, and a trunk portion, defining a second prosthesis lumen in fluid communication with said first prosthesis lumen, said trunk portion having, in its deployed state, a second diameter.

Further, the present invention concerns a catheter having loaded thereon such an endoluminal prosthesis and configured for placing said endoluminal prosthesis at a vessel bifurcation, said catheter comprising a catheter body, having a guide wire lumen, for accommodating a guide wire, and a graft actuator lumen, a constraining sheath, for keeping radially compressed therein said loaded endoluminal prosthesis, and a graft actuator, accommodated in said graft actuator lumen.

Still further, the present invention relates to a deployment system, comprising such a catheter and such an endoluminal prosthesis, loaded onto said catheter.

Even further, the present invention relates to a method for deploying such an endoluminal prosthesis at a vessel bifurcation, using such a deployment system, the method comprising the steps of a) introducing via a first branching vessel said deployment system into a vessel bifurcation,
b) opening or retracting the first constraining sheath in order to release the endoluminal prosthesis, and
c) advancing a trunk portion into a vessel of the vessel bifurcation.

Such an endoluminal prosthesis, catheter, deployment system and method are known for example from WO 00/053251 A1.

Endoluminal prostheses, catheters and deployment systems of the kind mentioned at the outset are of high medical relevance and commercial impact, being, in many cases, the prime treatment for aneurisms like the abdominal aortic aneurism.

An aneurism is a localized dilation of a blood vessel wall usually caused by degeneration of the vessel wall, for example caused by artherosclerosis. In such cases, the dilation of the blood vessel may ultimately result in a rupture of the vessel wall, causing severe hemorrhage.

Aneurisms most frequently occur in the aortic system, whereby abdominal aortic aneurisms, for example at the aortic and iliac bifurcation, are particularly life-threatening. An estimated 65% of patients suffering from the rupture of such aneurisms die from sudden cardiovascular collapse before arriving at the hospital. This is owing to the fact that large volumes of blood are constantly transported along the abdominal aorta, the rupture leading to instant and extensive blood loss into the surrounding body cavities and tissues.

Methods of treatment of aortic aneurisms exist for several decades. In these methods, usually, a fully artificial replacement, for example a stent-graft or a xenograft, is used to replace or exclude from the blood flow the part of the vessel featuring the aneurism. Such bifurcation grafts, which can be utilized for treating aneurisms at the aortic and iliac bifurcation, are known for example from U.S. Pat. No. 2,845,959. However, such devices have to be placed in open surgery, inflicting a high degree of trauma on the often already otherwise health-compromised patient.

During the past years, the development of surgical treatments has gradually concentrated on endoscopic techniques, which allow the treatment of for example the vessel system in a manner avoiding the larger part of the traumata associated with open surgery. In this connection, self-expanding or balloon-dilated stents and stent grafts have become increasingly relevant.

For deployment, the circumferentially compacted endoluminal prosthesis (i.e. the stent or stent graft) is advanced, using a catheter, through a blood-vessel towards the site of, for example, the aneurism, and is than inflated, thereby becoming anchored to the healthy vessel-walls proximal and distal to the site of the aneurism. The lumen of the prosthesis at this point replaces the lumen of the vessel, excluding the aneurismic lumen from the blood flow.

In the case of the placement of an endoluminal prosthesis at branched vessels, typically, several catheters are introduced into the vessel system from different access-points. The branching vessels are then supported by different endoluminal prostheses, connected to each other by frictional force or other mechanical connections.

The problem here is that the connections between different endoluminal prostheses are to some degree prone for developing endoleaks or even for complete disconnection, when subjected to the forces occurring during the remolding process of the aneurismic dilation or when subjected to the natural movements taking place inside the human body. In such cases, the protective function of the endoluminal prosthesis is heavily compromised, potentially entailing thrombus formation or vessel rupture.

In order to avoid such leakage problems, WO 00/053251 A1, mentioned at the outset, describes an endoluminal prosthesis with a one-piece graft, which endoluminal prosthesis is adjusted for the placement in the aortic and iliac bifurcation. Further, WO 00/053251 A1 describes a deployment system adapted for the placement of this endoluminal prosthesis.

This deployment system is adjusted for a single access deployment, necessitating only one surgical entry point into the vessel system.

For this purpose, the deployment system comprises a catheter with a catheter body and a constraining sheath, the endoluminal prosthesis being comprised in between the constraining sheath and the catheter body. The endoluminal prosthesis features a main tubular body, comprising a trunk portion to rest in the aorta, and a branching portion to rest in the ipsilateral iliac artery, and a side branch that is to rest in the contralateral iliac artery, which side branch, in its undeployed state, is folded to the side of the main tubular body.

After the known prosthesis has been introduced into the aortic and iliac bifurcation via the ipsilateral iliac artery, the endoluminal prosthesis is partially released by shifting the constraining sheath in longitudinal direction. The side branch of the endoluminal prosthesis is then inserted into the contralateral iliac artery by retracting the entire endoluminal prosthesis and the prosthesis is fully deployed. According to WO 00/053251 A1, the main tubular body of the endoluminal prosthesis extends in the ipsilateral iliac artery as well as in the aorta and is reinforced by stent elements. Similarly, the side branch, coming to rest in the contralateral iliac artery, is reinforced by shape memory stent material.

This principle, however, bears important disadvantages.

According to some embodiments of the endoluminal prosthesis according to WO 00/053251 A1, there exists a considerable difference in the geometry and structure of the stent elements reinforcing the branching portion of the main tubular body, resting inside the ipsilateral iliac artery, and stent elements reinforcing the side branch in the contralateral iliac artery.

This difference leads to differences in the circumferential rigidity of the parts of the endoluminal prosthesis. Such differences in circumferential rigidity however may lead to long-term difficulties such as migration and mechanical dislocation of either the branching portion of the main tubular body or the side branch. In this case, the probability of endoleaks, forming between the distal ends of the prosthesis and the vessel wall, is increased.

In the remaining embodiments of the endoluminal prosthesis according to WO 00/053251 A1, the deployment mechanism itself is mechanically highly complex and, therefore, is prone for defects and incorrect or incomplete deployment. Such incorrect or incomplete deployment may result in the complete failure of the operation, making necessary open surgery, or may at least aggravate the risk for the formation of endoleaks.

Moreover, at least one of the vessel branches downstream of the vessel bifurcation is completely obstructed for a certain amount of time during the process of deployment.

In case of mechanical failure of the complex deployment mechanism, this vessel will even remain blocked, until the entire deployment system is removed in open surgery.

Especially in case of larger vessels, this obstruction may put at risk the patient's health.

Furthermore, the system according to WO 00/053251 A1 is, owing to its mechanical complexity, expensive in manufacture.

SUMMARY OF THE INVENTION

In view of the above, it is an object of the present invention to improve the endoluminal prosthesis of the prior art such that the formation of endoleaks can be better prevented, that the obstruction of vessels by prosthesis material can be better avoided, and that on the other hand a more cost-effective and mechanically simple solution is provided.

According to the invention, this and other objects are achieved with an endoluminal prosthesis of the kind mentioned at the outset, in which said trunk portion is essentially free from reinforcing stent-material.

Within the scope of the present invention, a graft sleeve is understood to be a tube like structure formed from a woven mesh or molded material, the graft sleeve material comprising for example natural or artificial fibers, PTFE, EPTFE and/or other materials known in the art.

Further, according to the invention, the expression "upstream", with respect to a blood vessel, describes the direction opposing the blood flow, while the expression "down-stream" describes the direction following the blood flow.

The expression "proximal", with respect to a catheter, describes the direction towards a surgeon handling the catheter, while the expression "distal" describes the direction towards the catheter tip, facing away from the surgeon.

When the novel endoluminal prosthesis is deployed at a vessel bifurcation, the branching portion comes to rest within the two vessel branches downstream of the bifurcation, anchoring the endoluminal prosthesis to these vessels.

As the two branches of the novel endoluminal prosthesis have essentially identical stent segments, the circumferential rigidity of both branches of the branching portion is virtually identical. Hence, long term difficulties such as migration and mechanical dislocation of the branching portion are better avoided.

This way, the new endoluminal prosthesis prevents the formation of endoleaks.

Also, as soon as the branching portion is deployed, no prosthesis material obstructs the blood flow to both vessel branches downstream the vessel bifurcation. Presently, with the expression that the prosthesis comprises/has a one-piece graft sleeve, it is meant to express that the prosthesis represents one integral piece having a branching portion—which, in its deployed state, comes to rest within two vessel branches and which, thus, has in its deployed state two "branches" which are, nevertheless, formed integrally—and a trunk portion.

Hence, the blood flow to the vessel branches downstream the vessel bifurcation is interrupted only for a very brief period of time. Moreover, the blood flow is ensured even in case of malfunction of the deployment system, thus greatly reducing the patient's risk.

Further, the novel endoluminal prosthesis has the advantage that it allows a very compact folding. This is due to the virtual absence of stent material from the trunk portion, which, in its deployed state, is to rest in the main vessel upstream of the vessel bifurcation.

The fact, that the trunk portion is essentially free of stent material, at the same time enables an easy deployment of the trunk portion, which can be simply stretched along its longitudinal axis into the main vessel.

This way, only a comparably simple mechanical solution for the deployment of the trunk portion is required.

Hence, the new prosthesis allows the use of a deployment catheter with reduced mechanical complexity, reducing the risk of malfunctions and hence of incomplete or incorrect deployment of the endoluminal prosthesis.

The first diameter of the branching portion may be different from the second diameter of the trunk portion, the second preferably being larger than the first diameter.

Further, this way, the production costs of the endoluminal prosthesis are reduced.

The object of the invention is thus achieved completely.

According to one embodiment of the invention, the branching portion is reinforced by self-expandable stent elements.

When self-expandable stent elements are employed, anchoring the branching portion within the branching vessels does not require balloon expansion.

This has the advantage that the overall complexity of the catheter, required for deployment, can be reduced.

Further, the positioning and anchoring of the branching portion is brought about at the very beginning of the deployment procedure. Hence, the position of the endoluminal prosthesis is fixed early during the operation. The risk of migration of the endoluminal prosthesis in the further deployment process is thus reduced.

It is also preferred that the trunk portion comprises multiple corrugations.

Hereby, it is advantageous that such corrugations of the graft sleeve allow a large amount of graft sleeve material to be accommodated in comparably little space.

Thus, the diameter of the folded endoluminal prosthesis is reduced.

Further, it is preferred if the trunk portion, at its distal end, is reinforced in circumferential direction by a structural element.

The advantage hereby is that, after the endoluminal prosthesis has been fully deployed, the structural element may anchor the trunk portion to the main vessel at a position upstream of the aneurism, at least until an anchoring stent has been deployed within the trunk.

Also, such a structural element supports the deployment of the trunk portion, in that it keeps open a central opening, connecting the lumen of the trunk portion with the lumen of the main vessel.

Hence, the blood flow through the aorta is maintained throughout the entire deployment procedure at an even higher level.

Additionally, this way, the blood pressure from the main vessel will not—or only to a lesser degree—counteract the advancing of the trunk portion into the main vessel.

In this connection, it is further preferred if the structural element is an at least partially self-expandable stent.

Hereby, it is advantageous that no widening prior to deployment of the trunk portion is necessary. This further facilitates blood flow through the prosthesis throughout the operation.

It is also preferred, if the structural element comprises connection elements, to which a guide wire or catheter can be releasably connected.

Such connection elements may, for example, comprise connective pockets or loops, in which, for example, hooks can releasably engage.

This way, the structural element radially distributes the forces, exerted onto the trunk portion for extending it along its longitudinal axis, over the graft sleeve material. Hence, punctiform stress and thus damages of the graft sleeve can be avoided.

The present invention further concerns a catheter of the kind mentioned at the outset, which catheter is configured such that it can be kinked or curved in a region where the endoluminal prosthesis has its trunk portion, whereby the graft actuator lumen terminates in an opening at or proximal to that region.

The advantage of such a catheter is that an endoluminal prosthesis can be placed in such a way, that two branches of a branching portion come to rest within the two vessel branches downstream of the bifurcation, thereby anchoring the endoluminal prosthesis to these vessels. A further advantage is that the branches have essentially identical stent segments and thus an essentially identical circumferential rigidity.

Long-term difficulties, such as migration and mechanical dislocation, resulting from different circumferential rigidity of prosthesis branches in these vessels, can thus be avoided. Hence, the probability of endoleaks, forming between the distal ends of the prosthesis and the vessel wall, is greatly reduced.

Further, the mode of deployment, made possible by the novel catheter, ensures a more or less continuous blood flow throughout the deployment procedure.

Moreover, the novel catheter is mechanically less complex than the known solutions. This way, the novel catheter is less prone for malfunctions, decreasing the risk of incomplete or incorrect deployment of the endoluminal prosthesis. Hence, the probability of endoleaks can be reduced even more.

In addition, the reduced mechanical complexity has the advantage, that the production costs of the novel catheter are lower compared to known catheters of the kind mentioned at the outset.

It is preferred if the graft actuator at its distal end comprises a connecting portion adjusted to reversibly engaging the distal end of the trunk portion.

Such a connecting portion may, for example, be comprised of connective struts that lead from an essentially centred position, i.e. the position of the guide wire, to lateral positions, where the struts releasably engage the material of the endoluminal prosthesis.

The advantage hereby is, that a connecting portion, rather than the graft actuator itself, can engage the material at the distal end of the endoluminal prosthesis at several, radially distributed points. This way, the distal opening of the trunk portion can be aligned with the lumen of the main vessel.

Hence, a better blood flow can be maintained when advancing the trunk portion into the main vessel.

The catheter body, close to its distal end, may in an alternative embodiment be adjusted to at least temporarily forming a reverse curve.

Catheters adjusted to at least temporarily forming a reverse curve, for example pigtail catheters and Simmons sidewinder catheters, are known in the art.

Including the functionality of such a catheter into the novel catheter has the advantage that the deployment of the endoluminal prosthesis can be performed without the need for first placing a guide wire through the vessel bifurcation.

The present invention further relates to a deployment system of the kind mentioned at the outset, wherein said graft actuator of said catheter is releasably connected to a distal end of said trunk portion of said loaded endoluminal prosthesis.

Hence, by combining the features of the endoluminal prosthesis and the catheter according to the invention, a mechanically surprisingly simple solution is provided, which may be used for single access deployment of an endoluminal prosthesis in a vessel bifurcation.

The advantage of this system is that, owing to the relative mechanical simplicity, it is less prone for mechanical defects or malfunctions than known deployment systems for single access deployment of endoluminal prostheses at vessel bifurcations.

In this connection, it is further preferred if the graft actuator is releasably engaged in the distal end of the trunk portion of the endoluminal prosthesis, more preferably in the structural element at the distal end of the trunk portion, via a connecting portion.

Such a connecting portion, which, as described above, may be comprised of connective struts and may distribute the forces applied for extending the trunk portion, this way reduces the stress imposed on the material.

Further, because the distal opening of the prosthesis is aligned with the lumen of the main vessel, the trunk portion does not oppose the blood flow through the aortic vessel, reducing as well the resistance to be overcome in order to advance the trunk portion into the main vessel.

Further, this way, the structural element is kept in a position that is suitable for anchoring the trunk portion to the main vessel, for example the aorta.

It is further preferred, if the trunk portion of the loaded endoluminal prosthesis is compacted along its longitudinal axis.

The advantage here is, that even prior to the advancement of the trunk portion in the direction of a main vessel, the blood flow through both branches of the branching portion is open and unobstructed by prosthesis material.

Further, such a compaction along a longitudinal allows a large amount of graft sleeve material to be accommodated in comparably small space.

Further, it is preferred if the deployment system further comprises a second catheter loaded with a trunk reinforcing stent, preferably radially compressed in a constraining sheath.

Such trunk reinforcing stent preferably is a self-expandable stent, which can be deployed by standard catheters. Of course, in this connection, also balloon-expandable stents and corresponding standard balloon-catheters may be used.

The trunk reinforcing stent will serve to reinforce the trunk portion mechanically. Hence, the benefits of a fully mechanically supported endoluminal prosthesis can be accomplished with the novel endoluminal prosthesis as well. Moreover, the trunk reinforcing stent may also serve to anchor the distal end of the trunk within the aorta. Hence, mechanical dislocation of the trunk from the healthy parts of the aorta, upstream of the aneurism can be better avoided.

In this connection, the guide wire needs to be rerouted into the main vessel, in order to guide the second catheter.

Alternatively, the graft actuator may be used to insert into the main vessel the second catheter. Hence, no separate placement of a different guide wire is necessary.

Alternatively, the first catheter may at the same time serve as the second catheter.

In this connection, the portion of the catheter, carrying the trunk reinforcing stent, would be provided proximal to the portion of the catheter carrying the endoluminal prosthesis. According to this embodiment, the first catheter, after the deployment of the endoluminal prosthesis, is retracted beyond the bifurcation and then re-advanced into the main vessel. Then, the trunk reinforcing stent is deployed.

The advantage of combining the functionalities of endoluminal prosthesis deployment and stent deployment in the new catheter is that no catheter exchange is necessary in between deploying the endoluminal prosthesis and the trunk reinforcing stent. This results in an overall reduced operation time.

In this connection, it is also possible that the first constraining sheath at the same time serves as the second constraining sheath.

This modification serves to simplify the overall mechanical layout of the catheter. By using only a single constraining sheath that is retracted to a first position in order to release the endoluminal prosthesis and then, upon re-advancement of the catheter into the main vessel, is retracted into a second position, for deploying the stent, the number of movable parts in the catheter can be reduced. Moreover, this way the handling of the deployment system is simplified.

According to the present invention, it is also preferred, if the trunk reinforcing stent comprises a neck section, which assumes a diameter smaller than the diameter of the distal and proximal end of the neck section, and thus smaller than the diameter of main vessel, when the stent is fully expanded.

In this connection, the trunk reinforcing stent may be constituted of a preformed, shape memory material, such as nitinol. Alternatively, the neck section may be generated during balloon expansion of the stent, utilizing a balloon with a neck section. Further, the stent may be self-expanding, with the neck section being constricted to its smaller diameter by the material and/or mechanical construction of this stent section.

The advantage of such trunk reinforcing stent with a neck section is that obstruction of side vessels with narrow apertures can be avoided.

When a standard-stent is placed over the narrow aperture of a side vessel, eventually, the aperture will be obstructed by stent material.

By contrast, a stent with a neck section, the neck section being positioned over the aperture, prevents such blocking. In the area of the neck section, blood can freely access the space in between the stent material and the vessel wall through the struts and branches of the stent.

Hence, blood flow into or from the side vessel is not obstructed.

The "necked" stent portion can be made an integral part of the trunk reinforcing stent, at the distal end thereof, or can be a separate "anchoring" stent.

In view of this, the concept of such an anchoring stent is new and inventive on its own, as it can be used also with other grafts than the one-piece bifurcation graft of this application.

The present invention, further, relates to a method of the kind mentioned at the outset, wherein during step a), the deployment system is introduced in such way, that it comes to rest in the first branching vessel and the second branching vessel and forms a kink or curve at the location of the trunk portion juxtaposing a main vessel, and wherein during step c), the trunk portion is advanced into the main vessel.

The advantage of the novel method is that it allows employing an endoluminal prosthesis of the kind described above in luminal repair of a vessel bifurcation. Hence, the formation of endoleaks can be better prevented.

Further, using the novel method, the blood flow through the vessel bifurcation to be treated is essentially maintained throughout all steps of the operation.

According to one embodiment of the novel method, during step a), the deployment system is introduced into the vessel bifurcation using a guide wire.

In this connection, first, a guide wire is placed across the vessel bifurcation in both vessel branches downstream the vessel bifurcation. This crossover maneuver can be brought about utilizing catheters with curved ends such as pigtail- or Simmons sidewinder catheters. Such catheters are extensively known in the art.

After the guide wire has been placed, the deployment system is advanced into the vessel bifurcation using the Seldinger technique.

This way, the crossover of the deployment system can be performed in a simple and straightforward manner.

Alternatively, the crossover manoeuvre can also be performed without a guide wire, using a deployment system that includes a crossover functionality in the region of its distal end.

Further, in connection with the novel method, it is preferred if, during step c), the trunk portion is advanced by pushing forward the graft actuator.

The advantage here is that the trunk portion can be stretched and advanced into the main vessel in a manner, allowing the surgeon to tightly control the advancement process.

Further, it is preferred if, after step c), in a further step d), a trunk reinforcing stent is positioned and expanded in the region of the trunk portion and the main vessel, so that it anchors the endoluminal prosthesis to the main vessel and reinforces the endoluminal prosthesis along the trunk portion.

The advantage here lies in the fact that a separate stent is used for anchoring and reinforcing the endoluminal prosthesis, making possible the use of different stents, adapted to the respective individual needs of the patient.

Also, it is advantageous, that standard stents can be used for this purpose, further reducing the production costs of the deployment system.

It is, in this connection, also possible to employ two separate stents, fulfilling different functions. A first trunk reinforcing stent, deployed within the trunk portion, fulfils the function of structurally reinforcing the trunk, whereas a second, separate anchoring stent, deployed upstream of the reinforcing stent, fulfills the functions of anchoring the trunk to the aortic walls as well as sealing off the blood stream from the aneurismic lumen by pressing the trunk material against the aortic walls.

The trunk reinforcing stent and anchoring stent can also be placed such that they overlap at the distal end of the trunk reinforcing stent and the sealing section of the anchoring stent.

In the view of this, the separate invention, already mentioned above, concerns a stent for anchoring a tubular graft within a vessel, having a distal anchoring section and a proximal sealing section and in-between a neck section, the neck section, in the deployed state of the stent, having a diameter smaller than the diameter of the distal anchoring and proximal sealing sections of the stent.

According to a preferred embodiment, this stent may comprise a reinforcing section proximal to the sealing section, for reinforcing said tubular graft.

Further, the present invention concerns a kit comprising an endoluminal prosthesis and an anchoring stent of the kinds described above.

Still further, the separate invention concerns a respective method for anchoring a tubular graft in a vessel below apertures of side vessels, comprising the steps of putting in place the graft, and anchoring the graft using such an anchoring stent.

The neck section, in the deployed state of the stent, has a diameter smaller than the diameter of the distal anchoring and proximal sealing section of the stent, and thus smaller than the diameter a main vessel, wherein the stent is fully expanded.

Thus, such stent is suited to span a section of a main vessel where at least one side vessel branches off, such as the renal arteries branching off from the aorta. This stent can be used to anchor a tubular graft in an aneurism that lies very close to the openings of the side vessels so that a common stent would obstruct these openings.

Further advantages follow from the description and the attached drawings.

It goes without saying that the features mentioned above and those still to be explained below can be used not only in the respectively specified combinations, but also in other combinations or on their own, without departing from the scope of the present invention.

BRIEF DESCRIPTION OF THE DRAWINGS

Embodiments of the invention are illustrated in the Figures and explained in more detail in the following description. In the Figures.

DESCRIPTION OF PREFERRED EMBODIMENTS

Figure 1:
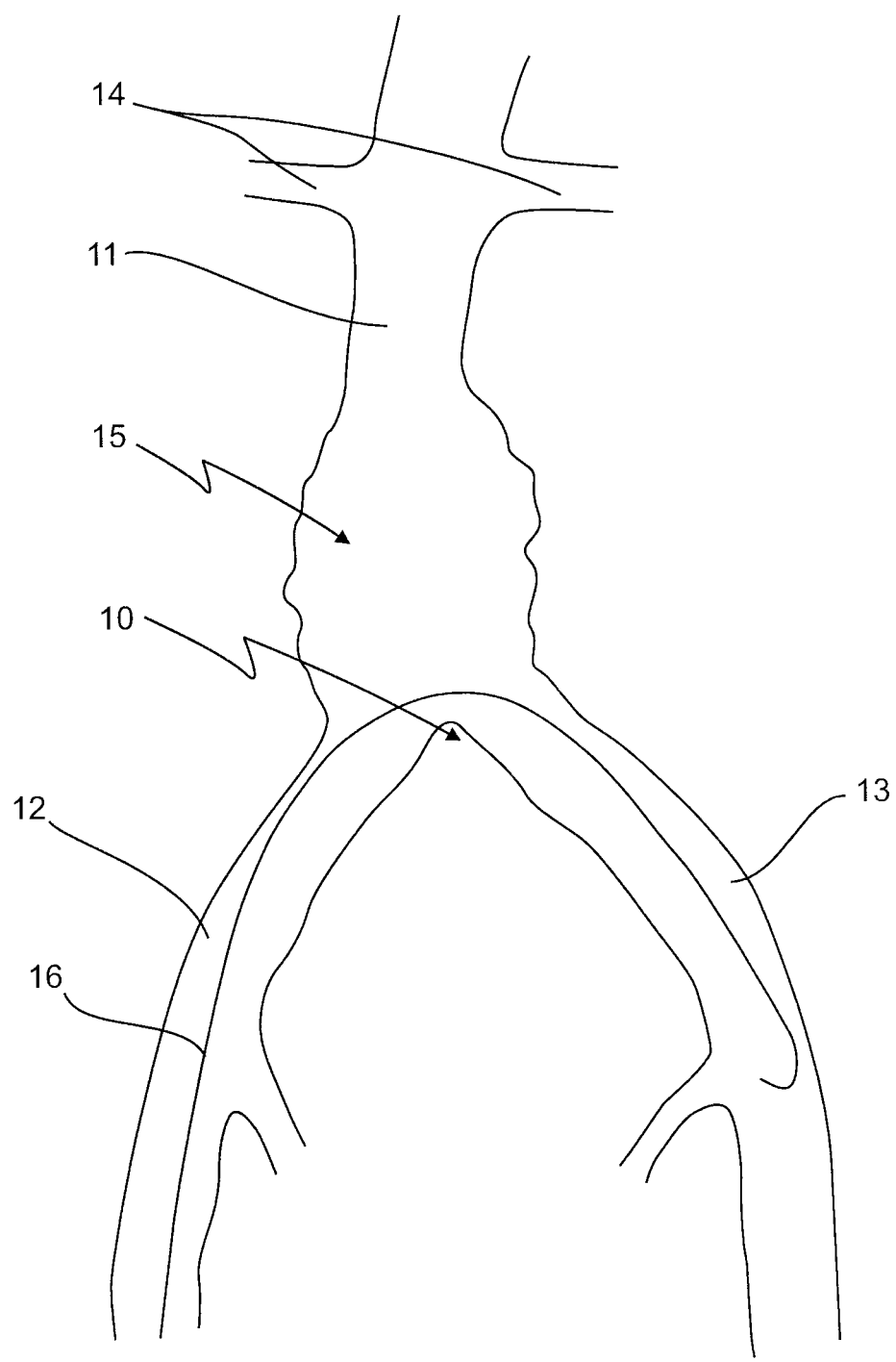
FIG. 1 shows in side view a schematic representation of the aortic and iliac bifurcation, a guide wire being inserted therein.

In FIG. 1, a schematic representation of an aortic and iliac bifurcation 10 is shown, comprising an aorta 11, an ipsilateral iliac artery 12 and a contralateral iliac artery 13. Proximal to the aortic and iliac bifurcation 10, two renal arteries 14 are shown, branching off from aorta 11. Distal to the renal arteries 14 and extending down towards the aortic and iliac bifurcation 10, aorta 11 shows an aneurism 15.

Further, a guide wire 16 is shown, which is inserted from the ipsilateral iliac artery 12 into the contralateral iliac artery 13, thereby crossing the aortic and iliac bifurcation 10.

The transition from the ipsilateral iliac artery 12 into the contralateral iliac artery 13 is achieved by a so called crossover-manoeuvre. Such crossover-manoeuvre is difficult to perform when using standard guide wires or catheters. This is therefore usually done by using guide wires or catheters with a bent tip, such as pigtail- or Simmons sidewinder catheters.

For this reason, the method for deploying an endoluminal prosthesis at the aortic and iliac bifurcation 10 comprises as a first step the placement of said guide wire 16 into the vessel bifurcation, i.e. from the ipsilateral iliac artery 12 into the contralateral iliac artery 13. For this purpose, for example, a catheter with a bent tip may be used.

Guide wire 16 will subsequently serve to advance a catheter into the vessel bifurcation 10, using the Seldinger technique.

Figure 2:
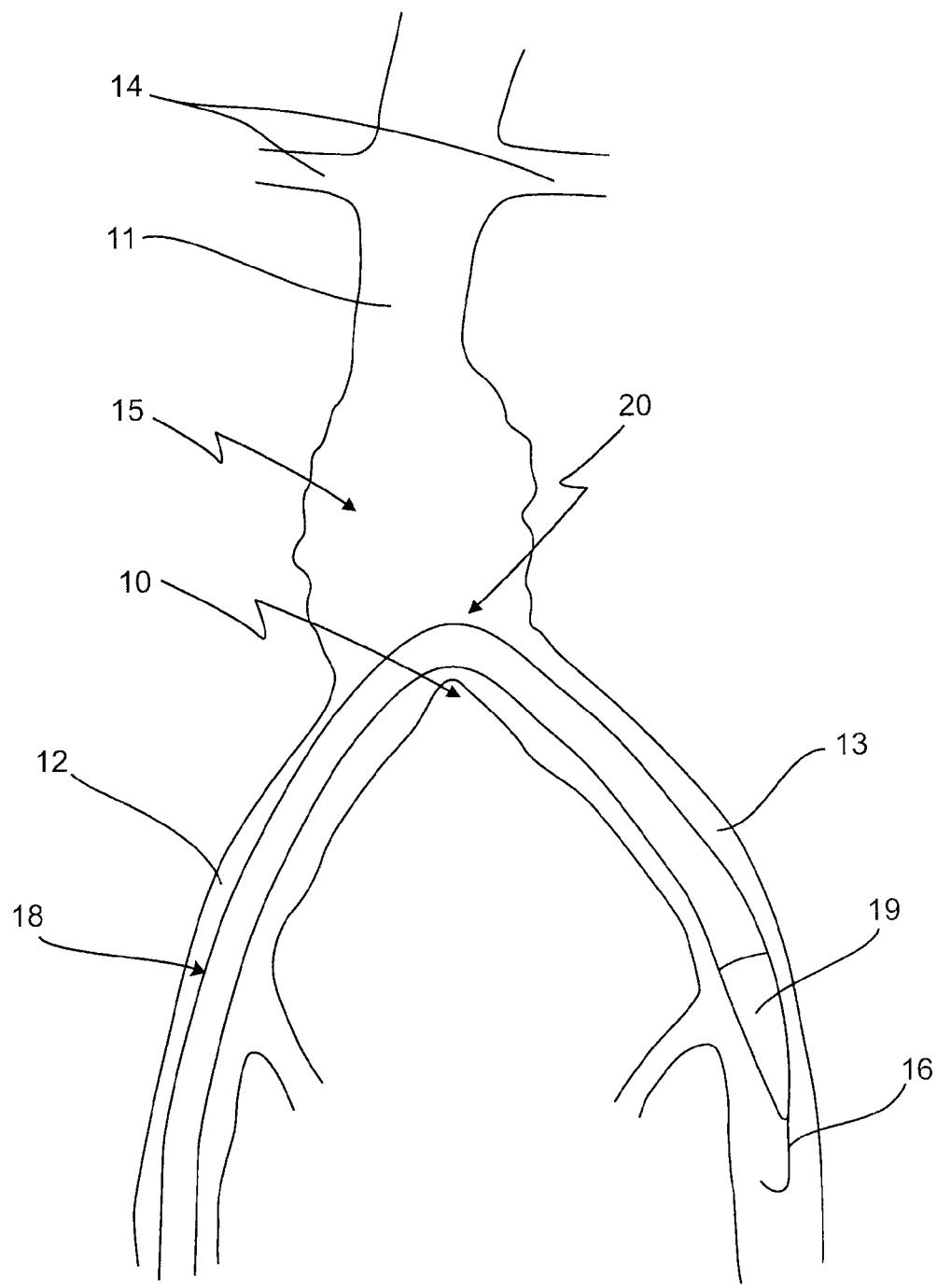
FIG. 2 shows the advancement of a catheter into the aortic and iliac bifurcation of FIG. 1.

In FIG. 2, a schematic side view representation of the aortic and iliac bifurcation 10 is shown, a catheter 18 having been inserted into the aortic and iliac bifurcation 10 via guide wire 16, such that catheter 18 extends from the ipsilateral iliac artery 12 into the contralateral iliac artery 13.

Catheter 18 comprises a nose cone 19 and a flexible region 20. Nose cone 19 serves the simpler and gentler passage of catheter 18 through the vessel system. The flexible region 20 of catheter 18 is sufficiently flexible to form a kink or curve, when catheter 18 is fully inserted into the aortic and iliac bifurcation 10.

Figure 3:
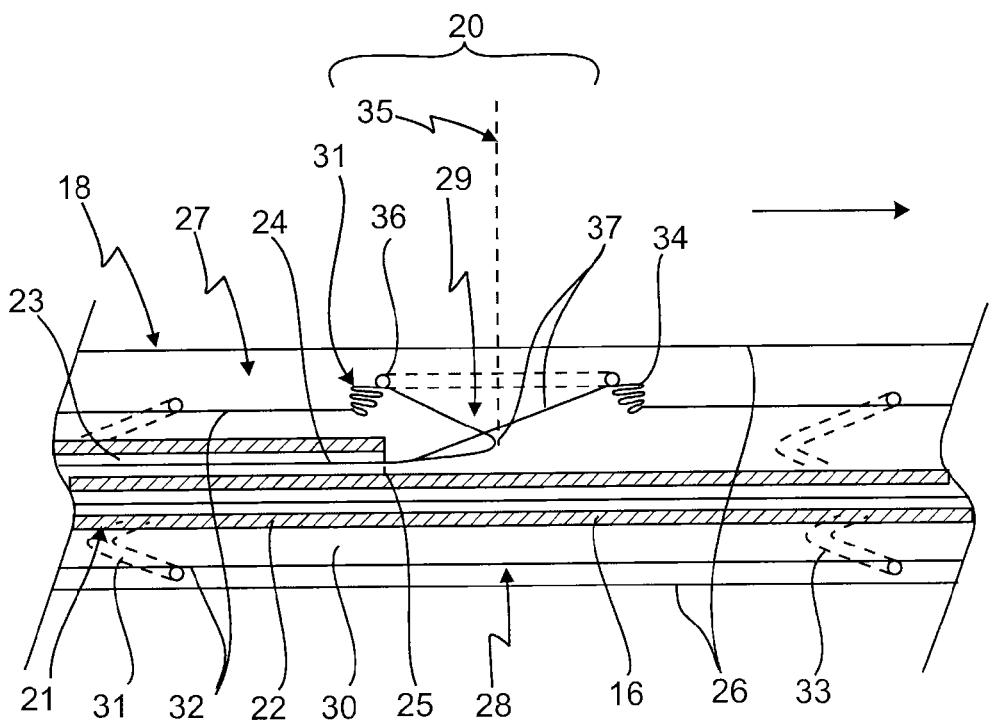
FIG. 3 shows in schematic sectional view a part of the catheter of FIG. 2, the catheter having an un-deployed endoluminal prosthesis.

FIG. 3 shows, in sectional side view, a section of catheter 18 around flexible region 20. An arrow in the upper right corner indicates the direction for advancing nose cone 19.

Catheter 18 comprises a catheter body 21 with a guide wire lumen 22 and a graft actuator lumen 23. Guide wire lumen 22 accommodates guide wire 16 whereas graft actuator lumen 23 accommodates a graft actuator 24. The graft actuator lumen 23 terminates in an opening 25 in region 20 of catheter 18.

An endoluminal prosthesis 27 is held in between the catheter body 21 and a constraining sheath 26.

The endoluminal prosthesis 27 comprises a branching portion 28 and a trunk portion 29. The branching portion 28 defines a first prosthesis lumen 30 whereas the trunk portion 29 defines a second prosthesis lumen 31, the branching portion 28 and the trunk portion 29 being formed from a one-piece graft sleeve 32 that is, in the region of the branching portion 28, reinforced by stent elements 33.

In the region of the trunk portion 29, the graft sleeve 32 has multiple corrugations 34, trunk portion 29 being compacted along its longitudinal axis 35. Further, trunk portion 29 has a proximal and a distal end, and is, at its distal end, reinforced by a structural element 36. The structural element 36 is connected to said graft actuator 24 via connective struts 37.

Figure 4:
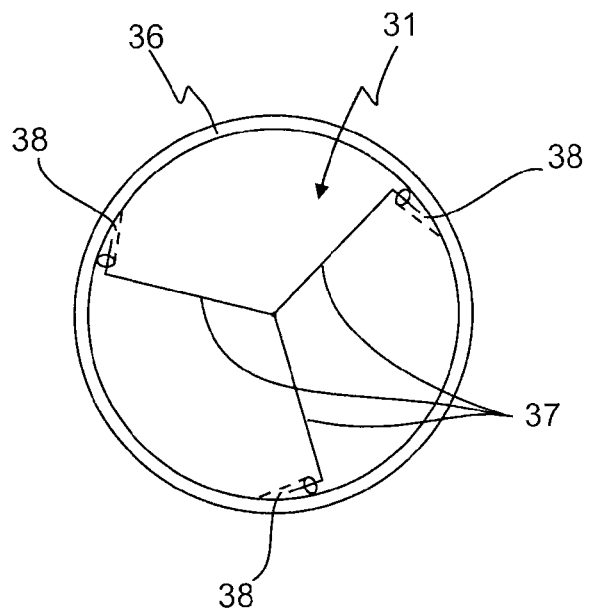
FIG. 4 shows in schematic front view a structural element of the trunk portion of the catheter of FIG. 3, with elements for releasably connecting thereto a graft actuator.

FIG. 4 shows, in front view and seen along axis 35 from FIG. 3, structural element 36 defining within its center the second prosthesis lumen 31 and further having connective pockets 38. The connective struts 37 releasably engage into connective pockets 38, thereby releasably connecting structural element 36 to the graft actuator 24 from FIG. 3.

Figure 5:
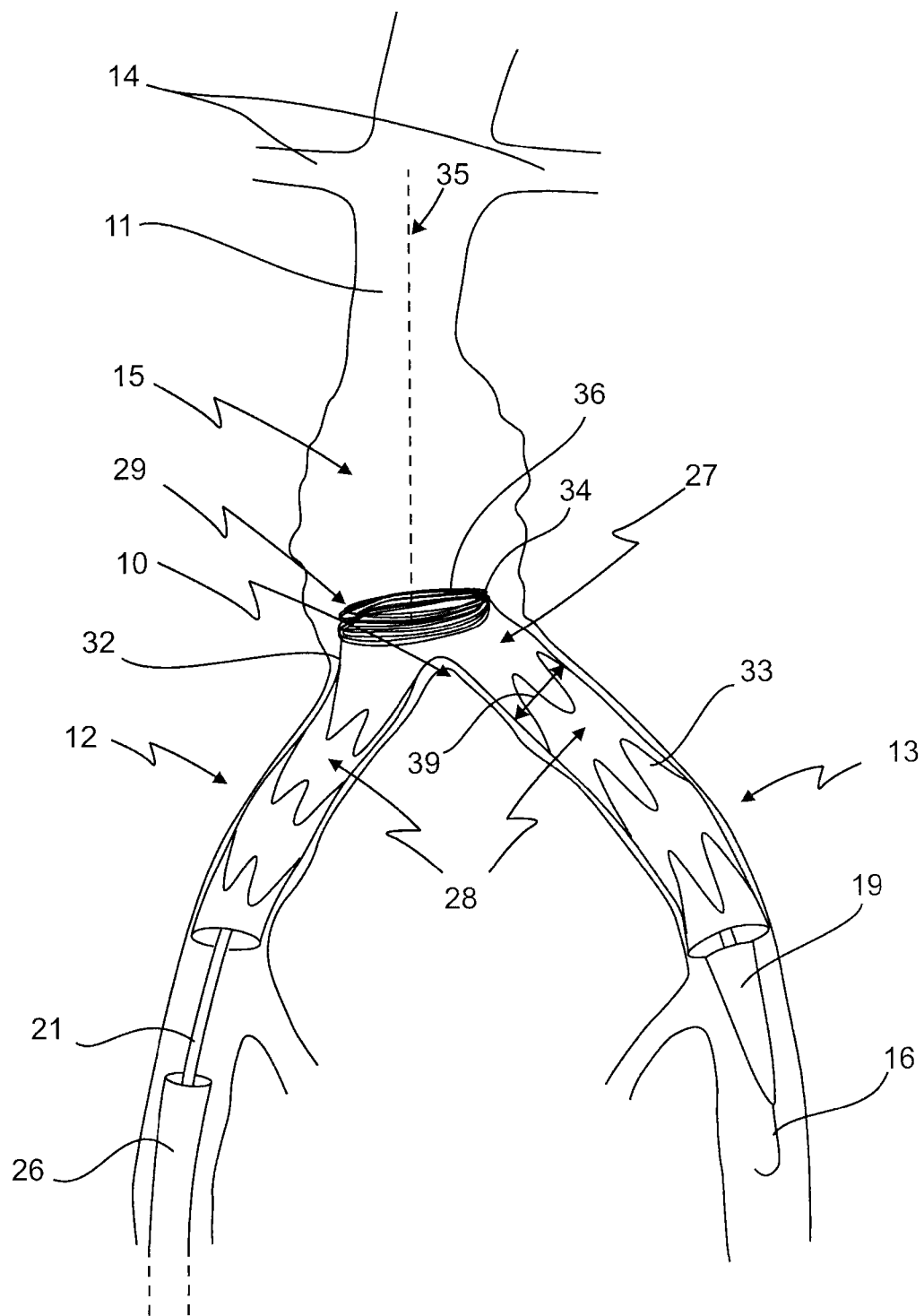
FIG. 5 shows in side view a catheter with an endoluminal prosthesis partially deployed inside the aortic and iliac bifurcation of FIG. 1.

FIG. 5 shows the representation of FIG. 2, but the constraining sheath 26 of catheter 18 now being fully retracted.

After retraction of constraining sheath 26, the branching portion 28, owing to the self-expansion of the stent elements 33, is fully deployed inside the ipsilateral iliac artery 12 and the contralateral iliac artery 13, covering as well the aortic and iliac bifurcation 10. The branching portion 28 now has assumed a first diameter 39.

Trunk portion 29 is still folded, resting on branching portion 28 and pointing towards aneurism 15 in aorta 11.

Figure 6:
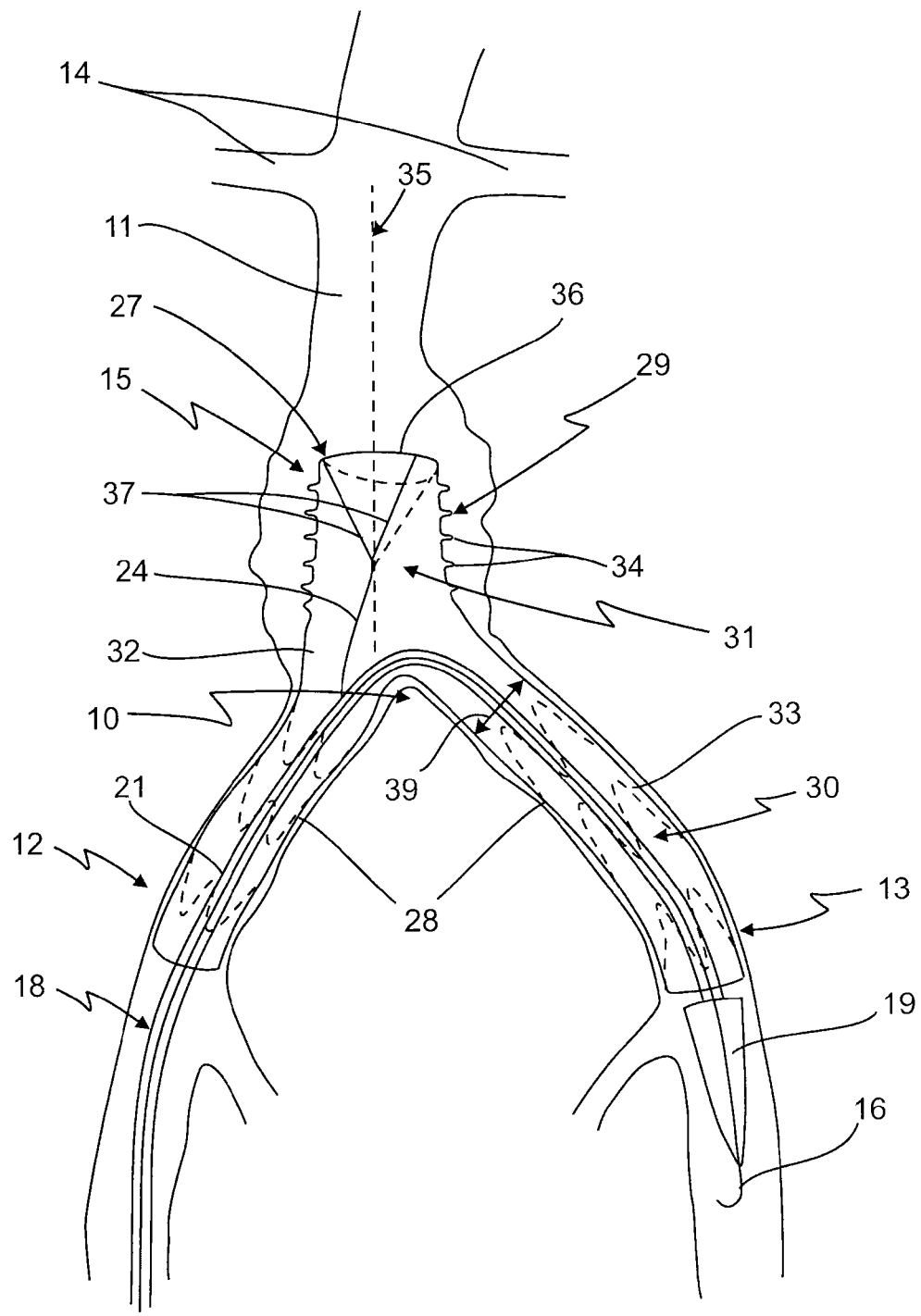
FIG. 6 shows the endoluminal prosthesis as in FIG. 5, the trunk portion now being partially deployed.

FIG. 6 shows the representation of FIG. 5, wherein trunk portion 29 is now being advanced into aorta 11.

After deployment of the branching portion 28, trunk portion 29 is stretched along its longitudinal axis 35 and advanced into aorta 11.

This movement is brought about by pushing forward, into the direction of the aorta 11, the graft actuator 24, which is connected to the structural element 36 via the connective struts 37.

Figure 7:
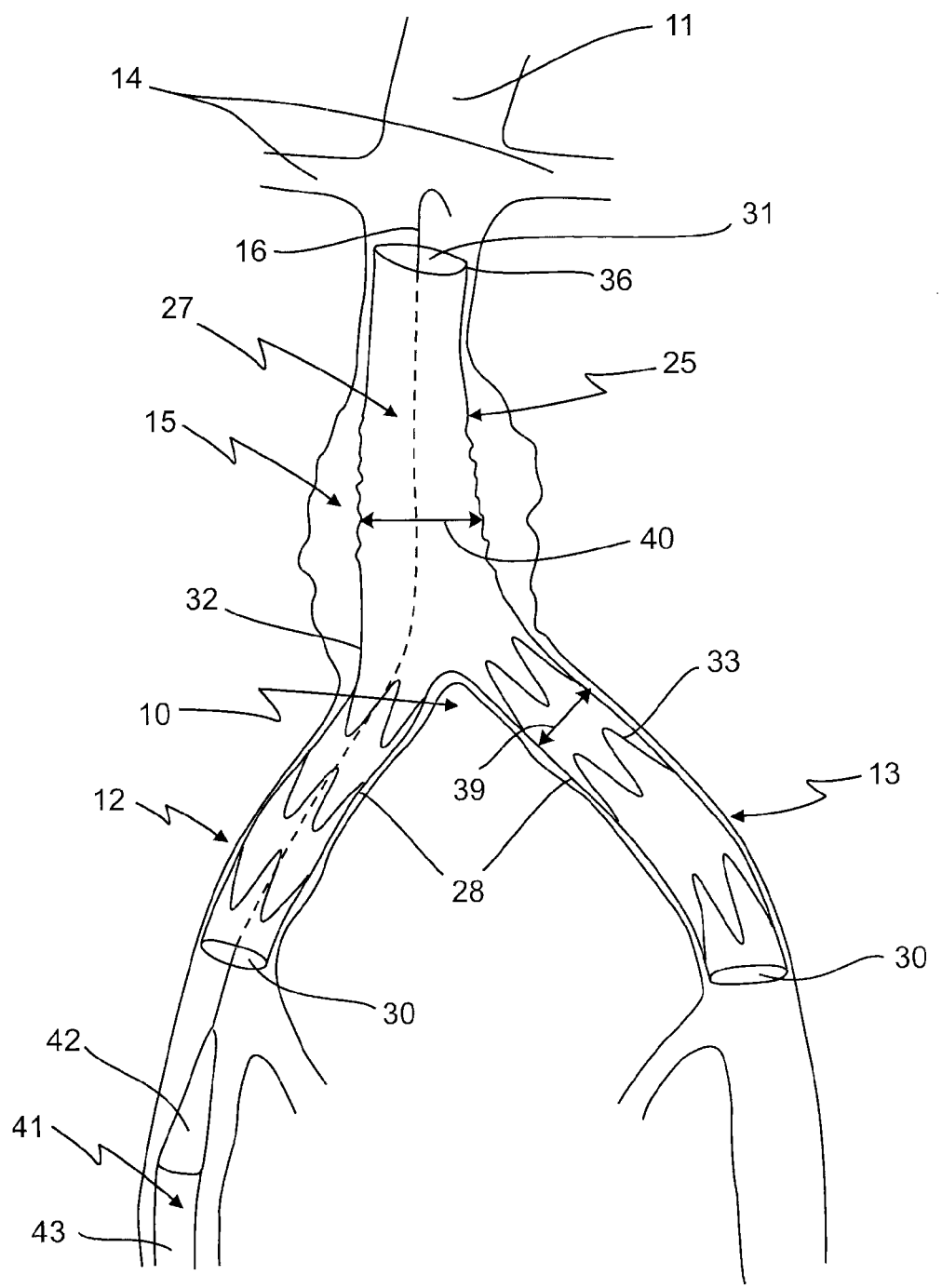
FIG. 7 shows the endoluminal prosthesis as in FIG. 6, but now being fully deployed, with the first guide wire being redirected into the aorta.

FIG. 7 shows the representation of FIG. 6, but trunk portion 29 now being fully advanced into aorta 11 and crossing aneurism 15.

Trunk portion 29 is anchored to aorta 11 by the structural element 36. The second prosthesis lumen 31 is now fully inflated and the trunk portion 28 assumes a second diameter 40. Second diameter 40, in this embodiment, is larger than first diameter 39 of branching portion 28.

At this point already, the endoluminal prosthesis 27 excludes the lumen of the aneurism 15 from the blood pressure. The first lumen 30 and the second lumen 31 functionally replace the damaged sections of the aorta 11, the ipsilateral iliac artery 12 and the contralateral iliac artery 13.

However, trunk portion 28, being essentially unsupported by stent material, is still very flexible and not able to withstand long term physical strain.

Therefore, a stent will now be inserted into trunk portion 28. For this reason, guide wire 16 has been partly withdrawn from contralateral iliac artery 13 and then pushed forward again, thereby being redirected into trunk portion 29 and, correspondingly, into aorta 11. A second catheter 41 with a nose cone 42 and a second constraining sheath 43 is inserted through the ipsilateral iliac artery 12 via guide wire 16.

Catheter 41 is used to deploy an aortic stent inside the second lumen 31 of the trunk portion 29 and inside aorta 11.

Figure 8:
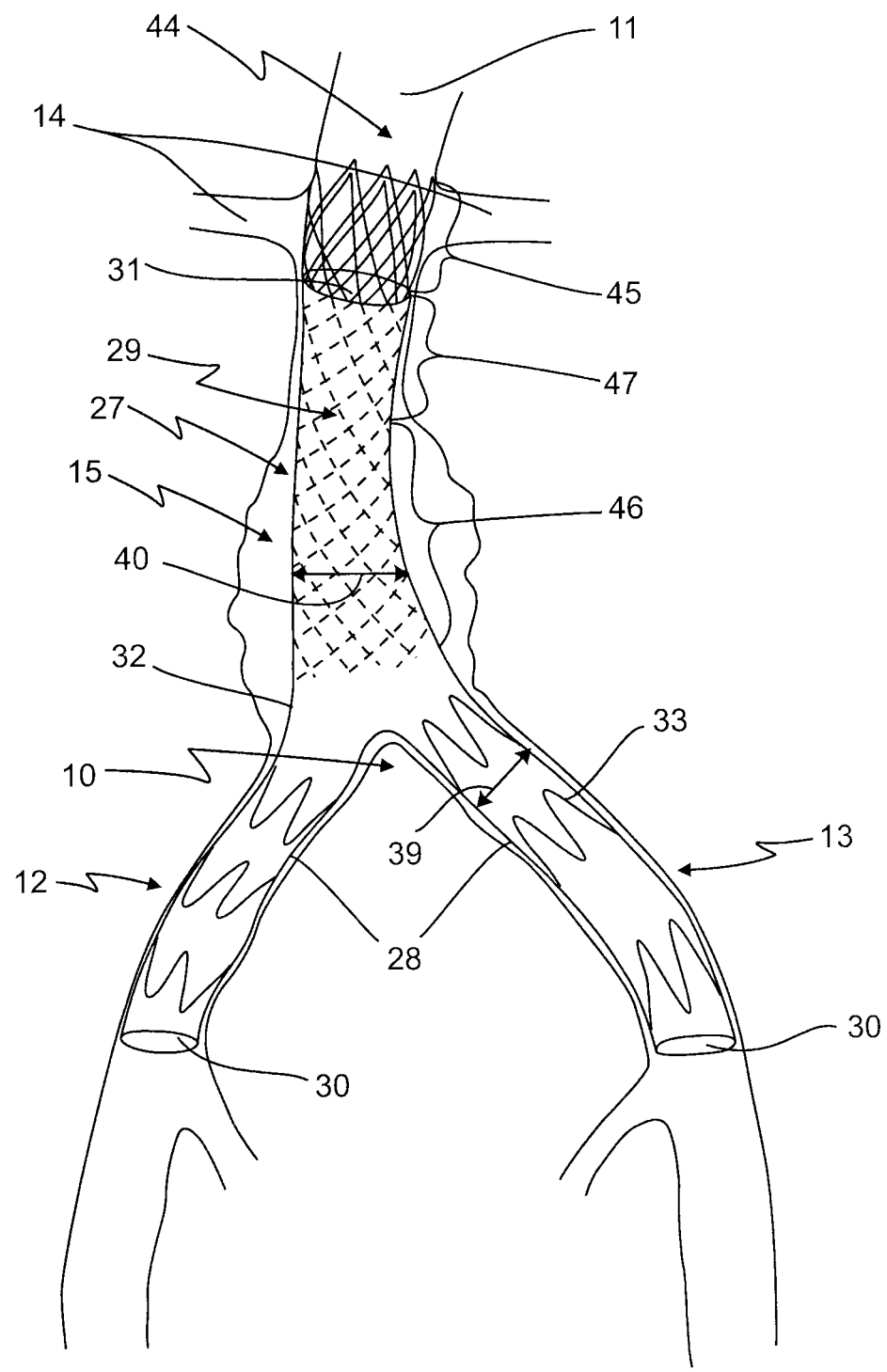
FIG. 8 shows the endoluminal prosthesis as in FIG. 7, the trunk portion being reinforced by a stent.

FIG. 8 shows the representation of FIG. 7, a trunk reinforcing stent 44 being deployed inside trunk portion 29 and aorta 11.

Upstream of trunk portion 29, a distal anchoring section 45 of trunk reinforcing stent 44 extends beyond the apertures between aorta 11 and renal arteries 14. In downstream direction, a proximal reinforcing section 46 of trunk reinforcing stent 44 extends to the transition between the trunk portion 29 and the branching portion 28. In-between distal anchoring section 45 and proximal reinforcing section 46, a sealing section 47 is provided, which, when trunk reinforcing stent 44 is placed, is located downstream of renal arteries 14 but upstream of aneurism 15.

Thereby, anchoring section 45 anchors the trunk portion 29 of the endoluminal prosthesis 27 to the healthy parts of the aorta 11 by frictionally engaging into the walls of aorta 11. Further, reinforcing section 46 structurally reinforces the trunk portion 29, in order for it to withstand long term physical strain. Moreover, sealing section 47, by frictionally engaging with the walls of aorta 11 and trunk portion 29, seals off the lumen of aneurism 15 from the blood flow and, additionally, anchors endoluminal prosthesis 27 to aorta 11.

Figure 9:
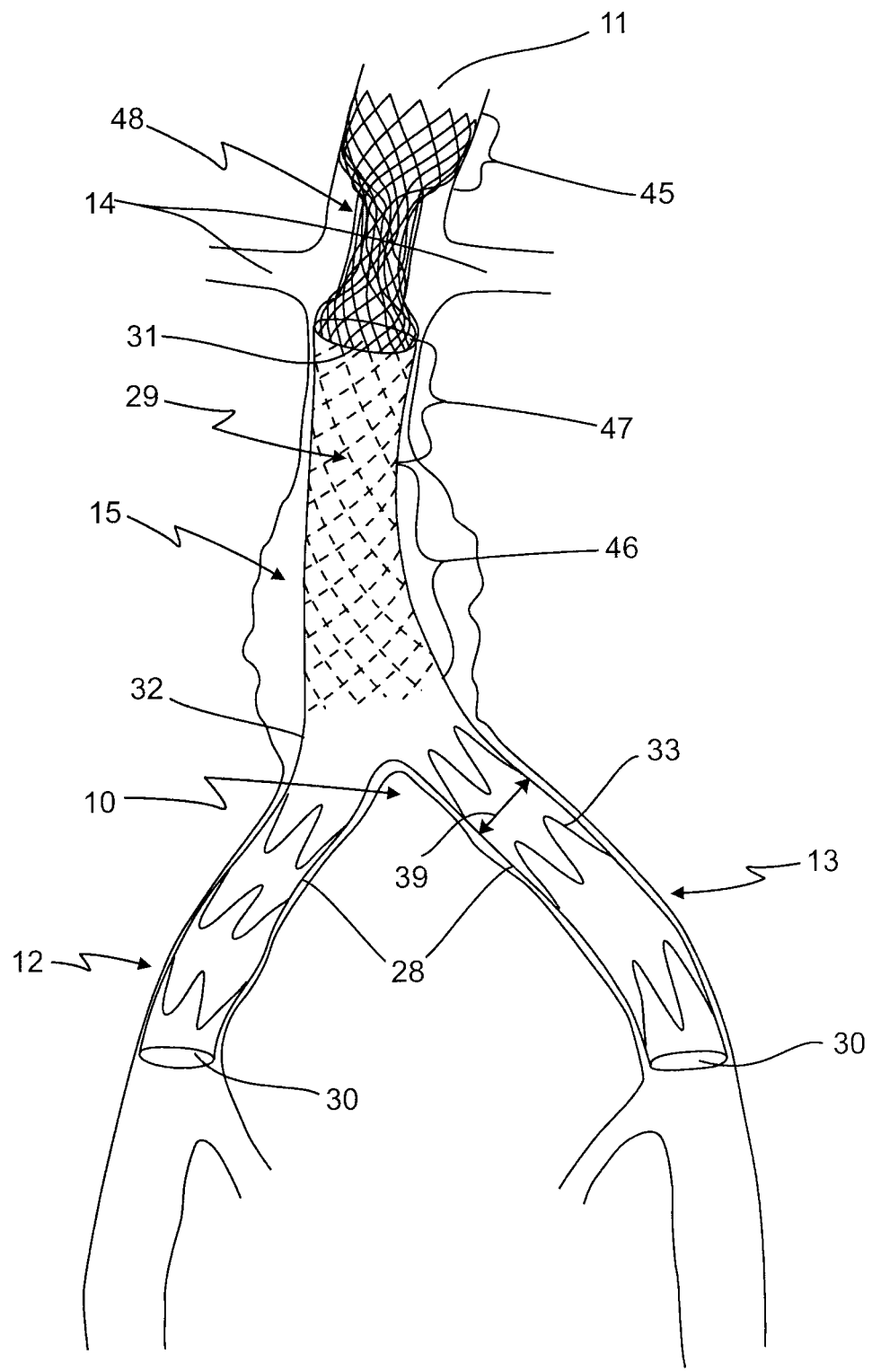
FIG. 9 shows the endoluminal prosthesis as in FIG. 8, but being reinforced by a stent according to an alternative embodiment.

FIG. 9 shows the representation of FIG. 8 with a trunk reinforcing stent 44' according to an alternative embodiment.

Trunk reinforcing stent 44', according to this alternative embodiment, comprises, in addition to distal anchoring section 45, proximal reinforcing section 46 and sealing section 47, a neck section 48. This neck section 48 has a diameter smaller than the diameter of distal anchoring section 45, proximal reinforcing section 46 and sealing section 47 of trunk reinforcing stent 44'.

Trunk reinforcing stent 44' is positioned in such way, that its neck section 48 is located in the region of the apertures from aorta 11 to renal arteries 14. Hence, while distal anchoring section 45, proximal reinforcing section 46 and sealing section 47 fulfil their functions as in the case of trunk reinforcing stent 44, the apertures between aorta 11 and renal arteries 14 remain unobstructed by stent material.

Figure 10:
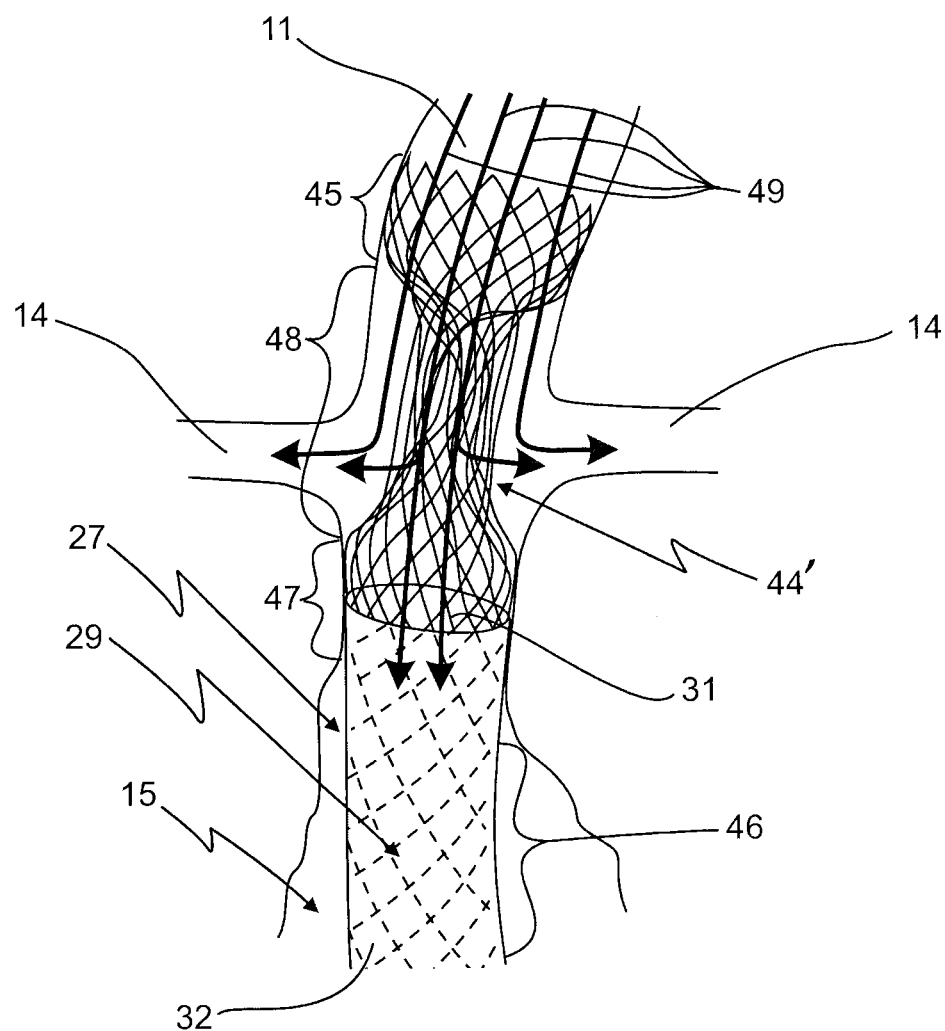
FIG. 10 shows an enlarged view of a stent as in FIG. 9.

FIG. 10 shows an enlarged view of trunk reinforcing stent 44', whereby aneurism 15 in FIG. 10 has an extension very close to renal arteries 14.

Trunk reinforcing Stent 44' comprises anchoring section 45, provided at the distal end of trunk reinforcing stent 44', neck section 48, provided proximal to anchoring section 45, sealing section 47, located proximal to neck section 48 and reinforcing section 46, located proximal to sealing section 47.

The longitudinal extension of sealing section 47 is smaller than with the stent 44' of FIG. 9. This is due to the fact that aneurism 15 here is very close to renal arteries 14. This might give rise to the problem that stent 44' cannot be anchored with a sufficient strength to the walls of aorta 11 just below the openings or apertures of renal arteries 14. However, due to upper anchoring section 45, stent 44' and thus graft sleeve 32 nevertheless is fixed against movement. This anchoring does not cover the apertures of renal arteries 14 due the neck section 48.

The function of neck section 48 is the maintenance of blood flow, indicated by arrows 49, from aorta 11 into renal arteries 14.

When using conventional stents, the renal arteries 14 may be obstructed by stent material.

By contrast, using stent 44', the stent material of neck section 48 is distanced from the aortic walls and, hence, from the apertures of aorta 11 into renal arteries 14.

Blood flow can take place through all meshes of aortic stent 44'. Blood thus enters the space in between the meshes of neck section 48 and the aortic walls.

Blood may, therefore, flow into renal arteries 14 either from above of renal arteries 14 and from outside of stent 44', i.e. between stent 44' and the aortic walls, or laterally out of stent 44' directly into renal arteries 14.

Blood flow into renal arteries 14 can therefore not be inhibited by stent material.

Further, the meshes of neck section 45 may be equal or even larger than in sealing and anchoring sections 46, 47.

Figure 11:
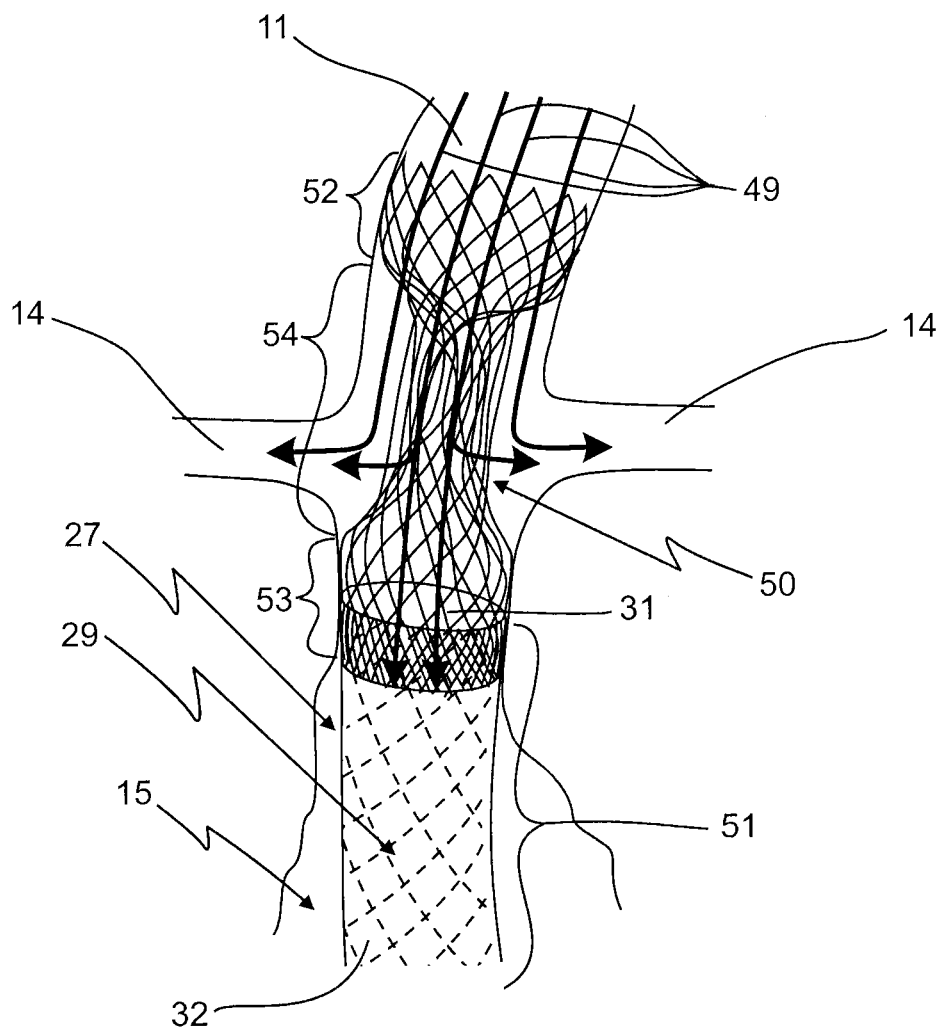
FIG. 11 shows a situation as in FIG. 10, a separate anchoring stent being used instead of a necked portion of the reinforcing stent.

FIG. 11 shows the representation of FIG. 10, but the trunk portion 29 now being anchored and reinforced by two separate stents, an anchoring stent 50 and a reinforcing stent 51.

Reinforcing stent 51, its major function being to structurally reinforce the trunk portion 29 of endoluminal prosthesis 27, may either be a self-expandable or balloon expandable standard stent.

Anchoring stent 50, however, comprises three sections, a distal anchoring section 52, a proximal sealing section 53 and a neck section 54, provided in-between distal anchoring section 52 and proximal sealing section 53.

Anchoring section 52 has the same function as anchoring section 45 in the case of trunk reinforcing stents 44 and 44', described above.

The function of anchoring section 52 is to anchor stent 50 and consequently endoluminal prosthesis 27 to aorta 11.

For this purpose, deployed anchoring section 52 assumes a diameter, corresponding to the diameter of aorta 11, and frictionally engages into the walls of aorta 11 in a fashion, known in the art.

Sealing section 53 has the same function as sealing section 47 in the case of trunk reinforcing stents 44 and 44' described above.

Accordingly, sealing section 53 fulfils a double-function. It frictionally engages into the walls of aorta 11, anchoring stent 50 and consequently endoluminal prosthesis 27 to the aortic walls. Further, it presses graft sleeve 32 against the aortic walls, forming a tight seal.

Thus endoluminal prosthesis 27 is secured from mechanical dislocation and the lumen of aneurism 15 is excluded from the blood flow.

Neck section 54 has the same function as neck section 48 in the case of trunk reinforcing stent 44', described above.

It maintains a certain distance between the apertures of aorta 11 to the renal arteries 14 and the stent material. Therefore, blood can freely flow into renal arteries 14.

Also in this case, the meshes of neck section 54 may be equal or larger than in sealing and anchoring sections 46, 47.

Anchoring stent 50 can be used not only in connection with prostheses 27 but also with other tubular grafts that need an anchoring stent that spans apertures of side vessels.

As shown in FIG. 11, anchoring stent 50 may, in this connection, be employed together with another stent.

Such combination may result in anchoring stent 50 and the other stent, in the present example trunk reinforcing stent 51, overlapping in the region of sealing section 53 of anchoring stent 50. Also, it is possible to deploy the stents such that no overlap occurs.

The combination of anchoring stent 50 with another stent leads to a greater flexibility in the use of anchoring stent 50 compared to, for example, trunk reinforcing stent 44', having as well a neck section 48. This, in the present example, is due to the possibility of employing reinforcing stent 51 in different lengths, thereby adjusting the total length of the stents (50, 51) to the distance between aortic and iliac bifurcation 10 and renal arteries 14, which length varies from patient to patient.

Hence, using anchoring stent 50, tubular grafts can efficiently be anchored to vessels even in proximity to branching off vessels.

What is claimed is:

1. A catheter having loaded thereon an endoluminal prosthesis, said endoluminal prosthesis comprising a one-piece graft sleeve, said graft sleeve having a branching portion defining a first prosthesis lumen, said branching portion having in a deployed state, a first diameter and is reinforced by self-expandable stent elements, a trunk portion defining a second prosthesis lumen in fluid communication with said first prosthesis lumen, said trunk portion having, in a deployed state, a second diameter wherein said trunk portion is essentially free from reinforcing stent-material, and wherein said catheter is configured for placing said endoluminal prosthesis at a vessel bifurcation, said catheter comprising a catheter body having a guide wire lumen for accommodating a guide wire and a graft actuator lumen, a constraining sheath for keeping radially compressed therein said loaded endoluminal prosthesis, and a graft actuator accommodated in said graft actuator lumen, wherein the trunk portion in a loaded state of the endoluminal prosthesis is compacted along a complete longitudinal axis and at a distal end has a reinforcing structural element wherein the catheter is configured such that it can be kinked or curved in a region where the loaded endoluminal prosthesis has the branching portion branching off from the trunk portion, wherein said graft actuator lumen terminates in an opening of the catheter body at the region where the loaded endoluminal prosthesis has the branching portion branching off from the trunk portion, and wherein the graft actuator on a distal end has connective struts releasably connecting the structural element of the trunk portion to the graft actuator.

2. A deployment system for deploying an endoluminal prosthesis in a vessel with a main vessel and two branching vessels, said deployment system comprising;

a catheter having loaded thereon an endoluminal prosthesis and configured for placing said endoluminal prosthesis at a vessel bifurcation, said catheter comprising a catheter body having a guide wire lumen for accommodating a guide wire and a graft actuator lumen; a constraining sheath for keeping radially compressed therein said loaded endoluminal prosthesis; and a graft actuator accommodated in said graft actuator lumen, wherein said catheter is configured such that it can be kinked or curved in a region where the loaded endoluminal prosthesis has a branching portion branching off from a trunk portion, said graft actuator lumen terminates in an opening of the catheter body at the region where the loaded endoluminal prosthesis has the branching portion branching off from the trunk portion, and wherein the graft actuator on a distal end has connective struts, and wherein said endoluminal prosthesis comprises a one-piece graft sleeve, said graft sleeve having the branching portion defining a first prosthesis lumen, said branching portion having in a deployed state a first diameter and being reinforced by stent elements; and the trunk portion defining a second prosthesis lumen in fluid communication with said first prosthesis lumen, wherein the trunk portion in a loaded state of the endoluminal prosthesis is compacted along a complete longitudinal axis, and wherein said trunk portion has, in a deployed state, a second diameter, a distal and a proximal end, wherein said trunk portion is essentially free from reinforcing stent-material, wherein said graft actuator of said catheter via said connecting struts is releasably connected to a distal end of said trunk portion of said loaded endoluminal prosthesis.

3. The deployment system of claim 2, wherein the graft actuator is releasably engaged in a structural element at the distal end of the trunk portion.

4. The deployment system of claim 2, further comprising a second catheter loaded with a trunk reinforcing stent.

5. The deployment system of claim 4, wherein the trunk reinforcing stent comprises a neck section which assumes a diameter smaller than a diameter of the distal and proximal end of the neck section when the stent is fully expanded.

6. A method for deploying an endoluminal prosthesis at a vessel bifurcation, the method comprising the steps of
a) introducing via a first branching vessel the deployment system as claimed in claim 2 into a vessel bifurcation,
b) opening or retracting the constraining sheath in order to release the endoluminal prosthesis, and
c) advancing the trunk portion into a vessel of the vessel bifurcation,
wherein during step a), the deployment system is introduced in such a way, that it comes to rest in the first branching vessel and a second branching vessel, and forms a kink or curve at the location of the trunk portion juxtaposing a main vessel, and wherein during step c), the trunk portion is advanced into the main vessel by pushing forward the graft actuator releasably connected to the distal end of the trunk portion.

7. The method as claimed in claim 6, wherein, during step a), the deployment system is introduced into the vessel bifurcation using a guide wire.

8. The method as claimed in claim 6, wherein, after step c), in a further step d), a trunk reinforcing stent is positioned and expanded in a region of the trunk portion and the main vessel, so that it anchors the endoluminal prosthesis to the main vessel and reinforces the endoluminal prosthesis along the trunk portion.

* * * * *